United States Patent [19]

Greven

[11] Patent Number: 4,491,579
[45] Date of Patent: Jan. 1, 1985

[54] PEPTIDES

[75] Inventor: Hendrik M. Greven, Almen, Netherlands

[73] Assignee: Akzo N.V., Arnhem, Netherlands

[21] Appl. No.: 547,438

[22] Filed: Nov. 1, 1983

[30] Foreign Application Priority Data

Nov. 10, 1982 [NL] Netherlands .......................... 8204346

[51] Int. Cl.³ ...................... A61K 37/00; C07C 103/52
[52] U.S. Cl. ............................... 424/177; 260/112.5 R
[58] Field of Search .................. 260/112.5 R; 424/177

[56] References Cited

U.S. PATENT DOCUMENTS 4,152,322 5/1979 Freidinger ................... 260/112.5 R Primary Examiner—Delbert R. Phillips
Attorney, Agent, or Firm—Abelman, Frayne, Rezac & Schwab

[57] ABSTRACT

The invention relates to polypeptides, in particular to penta- and hexapeptides, characterized by the general formula I:

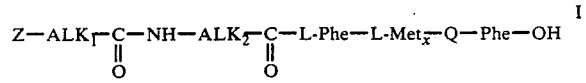

or a functional derivative thereof, wherein
Z represents hydrogen or $NH_2$,
$ALK_1$ represents an alkylene or alkylidene group having 1-6 carbon atoms,
$ALK_2$ represents an alkylidene group having 1-6 carbon atoms,
$Met_x$ represents the aminoacid radical Met, Met(O) or Met($O_2$) and
Q represents the aminoacid radical Lys or Arg, with the proviso that one of the aminoacid radicals Q and the C-terminal Phe is in the D-configuration and the other has the L-configuration.

5 Claims, No Drawings

PEPTIDES

The invention relates to polypeptides, in particular to penta- and hexapeptides, to a process for the preparation of these peptides and to pharmaceutical formulations which contain these peptides as the active ingredient.

More especially, the invention relates to an entirely new class of peptides having neuroleptic properties. This new class of peptides is characterized by the general formula I:

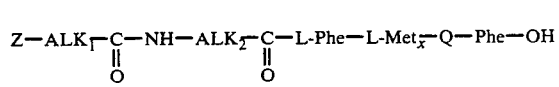

or a functional derivative thereof, wherein
Z represents hydrogen or $NH_2$,
$ALK_1$ represents an alkylene or alkylidene group having 1–6 carbon atoms,
$ALK_2$ represents an alkylidene group having 1–6 carbon atoms,
$Met_x$ represents the aminoacid radical Met, Met(O) or $Met(O_2)$ and
Q represents the aminoacid radical Lys or Arg, with the proviso that one of the aminoacid radicals Q and the C-terminal Phe is in the D-configuration and the other has the L-configuration.

Preferred peptides are those of the general formula I, wherein Q represents D-Lys and/or wherein Z is $NH_2$ and $ALK_1$ and $ALK_2$ are both a methylene group, or one is a methylene group and the other an ethylidene group, respectively.

The peptides and peptide derivatives according to the general formula I are prepared in a manner conventional for peptides. The commonest method for the preparation of the present peptides is to couple the required aminoacids by condensation, either in a homogeneous phase or with the aid of a so-called solid phase.

The homogeneous phase condensation can be carried out as follows:
(a) condensation of a compound (aminoacid or peptide) having a free carboxyl group and protected other reactive groups, with a compound (aminoacid, peptide or amine) having a free amino acid group and protected other reactive groups, in the presence of a condensation agent,
(b) condensation of a compound (aminoacid or peptide) having an activated carboxyl group and, optionally, protected other reactive groups, with a compound (aminoacid, peptide or amine) having a free amino group and, optionally, protected other reactive groups, and
(c) condensation of a compound (aminoacid or peptide) having a free carboxyl group and protected other reactive groups with a compound (aminoacid, peptide or amine) having an activated amino group and, optionally, protected other reactive groups,
after which, if desired, the protective groups are removed.

Activation of the carboxyl group can inter alia take place by converting the carboxyl group to an acid halide, an azide, an anhydride, an imidazolide or an activated ester, such as the N-hydroxysuccinimide, N-hydroxy-benztriazole or p-benztriazole or p-nitrophenyl ester.

The amino group can be activated by converting it to a phosphite amide or by employing the "phosphorazo" method.

The commonest methods for the above condensation reactions are: the carbodiimide method, the azide method, the mixed anhydride method and the method of activated esters, as described in "The Peptides", volume I, 1965 (Academic Press), E. Schröder and K. Lübke.

However, it is also possible to prepare compounds according to formula I by the "solid phase" method of Merrifield, described in J.Am.Chem. Soc. 85, 2149 (1963). The coupling of the aminoacids of the peptides to be prepared starts from the carboxy-terminal side. For this, a solid carrier is necessary, on which reactive groups are present or to which such groups can be attached. This carrier can be, for example, a copolymer of styrene and divinylbenzene having reactive chloromethyl groups, or a polymeric carrier which has been rendered reactive with hydroxymethyl or benzylamine groups.

If, for example, a carrier containing chloromethyl groups is employed, the bonding of the first α-amino-protected aminoacid to the carrier takes place via an ester bond. In the synthesis of the peptide according to formula I, this reaction thus gives:

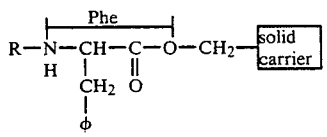

wherein R is an α-amino-protective group.

After removal of the group R, the subsequent α-amino-protected aminoacid (for example lysine, of which the ε-amino group is also protected) can be coupled by a condensation reaction, and after deprotecting the α-amino group the next aminoacid can be coupled on, etc.

After synthesis of the desired aminoacid sequence, the peptide is released from the carrier by means of, for example, liquid hydrogen fluoride, trifluoromethanesulphonic acid or methanesulphonic acid dissolved in trifluoroacetic acid. The peptide can also be removed from the carrier by transesterification with a lower alcohol, preferably methanol or ethanol, whereby a lower alkyl ester of the peptide is formed directly. Similarly, splitting with ammonia gives the amide.

The reactive groups which are not to participate in the condensation reaction are effectively protected, as stated, by groups which can again very easily be removed, for example by hydrolysis or reduction. Thus, a carboxyl group can be protected effectively by, for example, esterification with methanol, ethanol, tertiary butanol, benzyl alcohol or p-nitrobenzyl alcohol.

Groups which can effectively protect an amino group are usually acid groups, for example an acid group derived from an aliphatic, aromatic, araliphatic or heterocyclic carboxylic acid, such as acetic acid, benzoic acid or pyridinecarboxylic acid, or an acid group derived from carbonic acid, such as the ethoxycarbonyl, benzyloxycarbonyl, t-butoxycarbonyl or p-methoxy-benzyloxycarbonyl group, or an acid group derived from a sulphonic acid, such as the benzenesulphonyl or p-toluene-sulphonyl group, but other groups can also be used, such as substituted or unsubstituted aryl or aralkyl groups, for example benzyl and triphenylnethyl groups, or groups such as ortho-nitrophenylsulphenyl and 2-benzoyl-1-methylvinyl.

It is advisable also to protect the ε-amino group of lysine and the guanidine group of arginine. Conventional protective groups in this context are, for lysine, a tertiary-butoxycarbonyl group or a tosyl group, and for arginine a nitro or Mbs group (4-methoxybenzenesulphonyl).

The protective groups can be split off by various conventional methods, depending on the type of the group in question, for example with the aid of trifluoroacetic acid, or by mild reduction, for example with hydrogen and a catalyst, such as palladium, or with HBr in glacial acetic acid.

Peptides according to formule I, wherein $Met_x$ represents the aminoacid radical Met(O), can be prepared from the corresponding Met peptide by a mild oxidation known per se, for example with dilute hydrogen peroxide or a per-acid. Such as oxidation gives a mixture of the S- and R-sulphoxide, which mixture can be separated into the individual diastereoisomers in a manner known per se, for example by selective crystallisation. By using methionine-S-(or R-)sulphoxide in the peptide synthesis, the individual diastereoisomers can also be obtained directly.

The sulphone-peptides according to formula I, wherein $Met_x$ represents the acid radical $Met(O_2)$, can be obtained by oxidation of the corresponding Met-peptide I or by employing methionine-sulphone in the peptide synthesis.

By functional derivatives of the peptides according to the general formula I there are understood:
1. salts of the present peptides, in particular acid addition salts and metal salts;
2. $N^\alpha$-acyl derivatives, derived from an aliphatic carboxylic acid having 1-6 carbon atoms, preferably acetic acid;
3. amides or monoalkyl- or dialkyl-substituted amides, each alkyl having 1-6 carbon atoms, and
4. esters derived from alcohols having 1-18 C-atoms.

The acid addition salts can be obtained directly by isolating the peptide from the desired acid medium, or alternatively the peptide obtained can subsequently be converted to an acid addition salt by reaction of the peptide with an acid such as HCl, HBr, phosphoric acid, sulphuric acid, acetic acid, maleic acid, tartaric acid, citric acid, polyglutamic acid, carboxymethylcellulose etc.

The metal salts, in particular, the alkali metal salts, are obtained by reaction of the peptide with the desired metal base, such as NaOH, $Na_2CO_3$, $NaHCO_3$ etc.

$N^\alpha$-acyl derivatives are preferably prepared by using, in the peptide synthesis, an aminoacid in which the relevant $N^\alpha$-acyl group is already present. This acyl group then also functions as a protective group in the peptide synthesis. The desired $N^\alpha$-acyl derivative is in this way prepared direct. However, it is also possible to introduce the desired acyl group subsequently by acylating the peptide in the conventional manner.

The $N^\alpha$acyl group preferably used is the acetyl group.

In the homogeneous condensation method esters and amides are preferably prepared by employing in the peptide synthesis, an aminoacid which is already provided with the desired ester or amide group. They can however also be prepared by subsequently, esterifying the peptide obtained or converting it to an amide. In the "solid phase" method, esters can be obtained by transesterification of the peptide-carrier bond and amides can be obtained by treatment with ammonia.

Preferably, lower aliphatic esters derived from an alcohol having 1-6 C-atoms are employed, such as the methyl, ethyl, propyl, isopropyl, butyl, sec.-butyl, pentyl or hexyl esters.

Amides which are preferentially employed are unsubstituted amides, the monomethylamide or dimethylamide, or the monoethylamide or diethylamide.

As already mentioned above, the peptides according to the invention possess a neuroleptic activity, as a result of which they are, inter alia, suitable for the treatment of schizophrenia.

The peptides according to the invention can be administered parenterally, sublingually, intranasally, rectally or orally. Parenteral and intranasal administrations are to be preferred amongst these, since with such administrations the absorption of the peptide is greatest. The peptides are therefore preferably mixed with pharmaceutically acceptable auxiliaries which make the peptides suitable for parenteral or intranasal administration, resulting in solutions, suspensions (where appropriate via micro-encapsulation), emulsions and sprays.

Mixed with suitable auxiliaries the present peptides can also be employed in a form which is suitable for oral administration, such as pills, tablets and dragees. The present peptides can also be administered in the form of a suppository.

The peptides or peptide derivatives according to the invention are preferably employed in dosages of 1 μg to 5 mg per kg of body weight per day for parenteral administration. The recommended dosage for administration to human beings is between 0.3 and 30 mg, in particular between 1 and 10 mg per day. For intranasal and rectal administration the dosage is in general greater by a factor of 10-100 and for oral administration it is greater by a factor of 100-1,000.

The following is to be noted with respect to the examples which follow.

I. Where no optical configuration is mentioned, the L-form is meant.

II. The following abbreviations are used for the protective or activating groups employed:
Boc = tertiary-butoxycarbonyl
tBu = tertiary butyl
Me = methyl
ONp = p-nitrophenoxy
Z = benzyloxycarbonyl
Fmoc = 9-fluorenylmethoxycarbonyl
Ac = acetyl III. The following abbreviations are used for the solvents or reagents employed:
To = toluene
EtOH = ethanol
BuOH = butanol
Py = pyridine
HOAc = acetic acid
EtOAc = ethyl acetate
tBuOH = tert.-butanol
DMF = dimethylformamide
DCC = dicyclohexylcarbodiimide
DCU = dicyclohexylurea
TFA = trifluoroacetic acid
Wa = water
HOBt = N-hydroxybenztriazole IV. The following abbreviations are used for the aminoacid groups:
Met=methionyl
Met(O)=sulphoxide of methionyl
Met(O$_2$)=sulphone of methionyl
Phe=phenylalanyl
Lys=lysyl
Gly=glycyl
Arg=arginyl
Ala=alanyl
β-Ala=β-alanyl
Val=valyl.

EXAMPLE 1

Synthesis of H-Gly-Gly-Phe-Met-D-Lys-Phe-OH (1) Boc-Gly-Gly-Phe-Met-OH

This peptide is obtained as described in Rec. Trav.-Chim. Pays-Bas 99, 63 (1980).

(2) H-Gly-Gly-Phe-Met-D-Lys-Phe-OH

The protected dipeptide Z-D-Lys(Boc)-Phe-OtBu was freed from the protective group Z before coupling with the peptide obtained under 1(1). For this purpose, the dipeptide was dissolved in DMF, after which Pd/C catalyst (10% strength) was added and H$_2$ was passed through the mixture until no further CO$_2$ was liberated. Thereafter, the catalyst was filtered off.

The peptide obtained under 1(1), as well as 1.1 equivalents of DCC and 2 equivalents of HOBt, were added to the thus deprotected peptide H-D-Lys(Boc)-Phe-OtBu, after which the reaction mixture was stirred for 2 hours at 0° C. and then for 12 hours at room temperature. The precipitate of DCU was then filtered off, the filtrate was evaporated down and the residue was recrystallised from an EtOH/EtOAc (1:2) mixture. The Rf of this protected peptide in To/EtOH (4:1) was 0.73.

This peptide was freed from the protective groups in 90% TFA plus anisole under a stream of N$_2$ gas, after which ether was added and the precipitate was filtered off and again dissolved in a t-BuOH/Wa mixture (1:1). An ion exchanger in the acetate form (LEWATIT) was added subsequently and the mixture was stirred for 40 minutes. Thereafter, the ion exchanger was filtered off and the filtrate was purified by counter-current distribution in a BuOH/HOAc/Wa (4:1:5) mixture.

Rf in BuOH/Py/HOAc/Wa (8:3:1:4)=0.64.

EXAMPLE 2

Synthesis of H-Gly-Gly-Phe-Met-D-Arg-Phe-OH (1) Boc-Gly-Gly-Phe-Met-OH

This has already been described in Example 1(1).

(2) Z-D-Arg(NO$_2$)-Phe-OtBu

Equimolar quantities of Z-D-Arg(NO$_2$)-OH and H-Phe-OtBu were dissolved in DMF and coupled by adding DCC and HOBt under the conditions described in Example 1(2), DCU was filtered off, and the organic EtOAc layer of the filtrate was then extracted successively with acid, base and water, dried and crystallized from EtOAc-hexane mixture. The peptide subsequently purified with the aid of an SiO$_2$ column has an Rf of 0.52 in To/EtOH (4:1).

(3) H-Gly-Gly-Phe-Met-D-Arg-Phe-OH

The peptide obtained in Example 2(2) was hydrogenated and coupled with the peptide obtained under 2(1), and the coupling product was subsequently freed from protective groups in the manner described in Example 1(2).

The hexapeptide thus obtained was purified on an SiO$_2$ column, with the aid of a BuOH/Py/HOAc/Wa (20:3:1:4) mixture and has an Rf value of 0.46 in a BuOH/Py/HOAc/Wa (8:3:1:4) mixture.

EXAMPLE 3

Synthesis of H-Gly-Gly-Phe-Met-Lys-D-Phe-OH (1) Z-Lys(Boc)-D-Phe-OtBu

This peptide was prepared by coupling Z-Lys(Boc)-OH with H-D-Phe-OtBu in the presence of a DCC/HOBt mixture in the manner described under 1(2), and recrystallised from ether/petroleum ether (1:3). Rf=0.60 in a To/ether (4:1) mixture.

(2) H-Gly-Gly-Phe-Met-Lys-D-Phe-OH

The peptide obtained according to (1) was hydrogenated and coupled with Boc-Gly-Gly-Phe-Met-OH, freed from protective groups and purified as described in Example 1(2).

The hexapeptide thus obtained has an Rf of 0.40 in a BuOH/Py/HOAc/Wa (8:3:1:4) mixture.

EXAMPLE 4

The following peptides are prepared in a similar manner to that described in Examples 1–3:
H-Ala-Gly-Phe-Met-D-Lys-Phe-OH
H-Gly-Ala-Phe-Met-D-Lys-Phe-OH
H-Val-Gly-Phe-Met-D-Lys-Phe-OH
H-Gly-Gly-Phe-Met-D-Lys-Phe-NH$_2$
H-Gly-Gly-Phe-D-Lys-Phe-OMe
Ac-Gly-Phe-Met-D-Lys-Phe-OH
β-Ala-Gly-Phe-Met-D-Lys-Phe-OH.

EXAMPLE 5

Synthesis of H-Gly-Gly-Phe-Met(O)-D-Lys-Phe-OH 1.0 g (1.34 millimols) of H-Gly-Gly-Phe-Met-D-Lys-Phe-OH was dissolved in 80 ml of acetic acid, after which 10 equivalents (13.4 millimols) of hydrogen peroxide were added (as a 30 percent strength aqueous solution).

After the reaction mixture has been stirred for about 30 minutes at room temperature, freshly prepared platinum was added. To prepare this platinum catalyst, 5.4 g of PtO$_2$ were suspended in acetic acid and hydrogen and nitrogen were passed through the suspension for 30 minutes.

After having been stirred for 15 minutes, the reaction mixture was filtered and the filtrate was evaporated down. The residue was purified by counter-current distribution in a BuOH/HOAc/Wa (4:1:5) mixture. The yield was 600 mg.

Rf=0.26 in 1-BuOH/Py/HOAc/Wa mixture (8:3:1:4).

EXAMPLE 6

Synthesis of H-Gly-Gly-Phe-Met(O$_2$)-D-Lys-Phe-OH 1.0 g (1.34 millimols) of H-Gly-Gly-Phe-Met(O$_2$)-D-Lys-Phe-OH was dissolved in 10 ml of Wa and 0.14 ml of (70% strength) HCLO$_4$. 2.2 Equivalents of hydrogen peroxide and 10 mg of (NH$_4$)$_6$Mo$_7$O$_{24}$.4H$_2$O were added. After the mixture had been stirred for about 2 days, excess hydrogen peroxide was destroyed by adding NaHSO$_3$, after which the pH was brought to 7 and the solution was freeze-dried.

The peptide obtained was partially purified by counter-current distribution in a 1-BuOH/HOAc/Wa mixture (4:1:5).

800 mg of the product thus obtained were further purified on an SiO2 column, using a 1-BuOH/Py-/HOAc/Wa mixture (8:3:1:4) as the mobile phase.

Rf=0.33 in the above-mentioned 1-BuOH/Py-/HOAc/Wa mixture.

EXAMPLE 7

The following were prepared in a manner corresponding to that described in Examples 5 and 6:
Ac-Gly-Phe-Met(O)-D-Lys-Phe-OH,
H-Gly-Gly-Phe-Met(O)-Lys-D-Phe-OH,
H-Gly-Gly-Phe-Met(O2)-Lys-D-Phe-OH.

EXAMPLE 8

Synthesis of H-Gly-Gly-Phe-Met-D-Lys-Phe-OH by means of "solid phase" technique (1) Preparation of the resin for the solid phase Starting from the chloromethylated copolymer of styrene and 1% of divinylbenzene, the corresponding p-hydroxybenzyl alcohol resin was prepared in accordance with the method described by S. S. Wang (J.Amer.Chem.Soc. 95, 1328 (1973)).

(2) Fmoc-Phe-[solid carrier]

10.9 millimols of Fmoc-Phe-OH dissolved in 40 ml of DMF were coupled to 10 g of the resin (7 millimols) prepared according to 8(1) in 160 ml of methylene dichloride, in accordance with the method of Meienhofer et al. described in Int.J. Peptide Protein Res. 13, 35–42 (1979).

(3) Boc-Gly-Gly-Phe-Met-D-Lys(Boc)-Phe-[solid carrier]

Starting from Fmoc-Phe-[solid carrier], the protected aminoacids Fmoc-D-Lys(Boc)-OH, Fmoc-Met-OH, Fmoc-Phe-OH, Fmoc-Gly-OH and Boc-Gly-OH were coupled on, successively. The removal of the protective groups and the coupling were carried out as described below for the last coupling stage, namely of Boc-Gly-OH to H-Gly-Phe-Met-D-Lys(Boc)-Phe-[solid carrier].

10 g of Fmoc-Gly-Phe-Met-D-Lys(Boc)-Phe-[solid carrier] were freed from the protective Fmoc group by successively washing 3 times with 60 ml of DMF, twice with 60 ml of 50% strength piperidine in DMF, twice with 60 ml of dioxane/Wa (2:1) and 6 times with 60 ml of DMF.

6.6 millimols (3 equivalents) of Boc-Gly-OH and 3 equivalents of DCC and HOBt were added to the deprotected product. After the end of the coupling reaction, the peptide-resin was washed successively with 60 mlf of EtOH and 60 ml of DMF.

(4) Removal of the peptide from the solid carrier 11 g of the product described above were washed with 60 ml of methylene dichloride and then introduced into 70 ml of TFA/methylene dichloride (1:1) to which 0.1 ml of thioanisole had been added.

After 2 hours, the solid phase was filtered off and washed with 10% strength HOAc.

The filtrate was evaporated to dryness in vacuo and the residue, dissolved in 30 ml of tBuOH/H2O, was subsequently subjected to exchange with an ion exchanger in the acetate form.

Thereafter, the mixture was filtered and the filtrate was evaporated to dryness in vacuo.

The residue was purified on a SiO2 column, using a 1-BuOH/Py/HOAc/Wa mixture (8:3:1:4). The yield was 0.27 g.

I claim:

1. A peptide having the general formula:

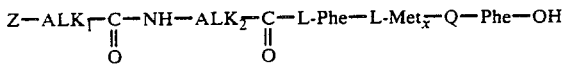

or a functional derivative thereof, wherein
Z represents hydrogen or amino,
$ALK_1$ represents an alkylene or alkylidene group having 1–6 carbon atoms,
$ALK_2$ represents an alkylidene group with 1–6 carbon atoms,
$Met_x$ represents the aminoacid radical Met, Met(O) or Met(O2) and
Q represents the aminoacid radical Lys or Arg, with the proviso that one of the aminoacid radicals
Q and the C-terminal Phe is in the D-configuration and the other has the L-configuration.

2. A peptide according to claim 1, wherein Q is the aminoacid radical D-Lys.

3. A peptide according to claim 1, wherein Z is the $NH_2$ group and $ALK_1$ and $ALK_2$ are both a methylene group.

4. A peptide according to claim 1, wherein $Met_x$ represents the aminoacid radical Met(O) or Met(O2).

5. A pharmaceutical composition for use as a neuroleptic agent which comprises a neuroleptic effective amount of a peptide as defined in any one of claims 1 to 4 and a pharmaceutically acceptable carrier.

* * * * *